United States Patent
Ueno

(10) Patent No.: US 7,557,928 B2
(45) Date of Patent: Jul. 7, 2009

(54) APPARATUS USING OPTICAL COHERENCE TOMOGRAPHY BASED ON SPECTRAL INTERFERENCE, AND AN OPHTHALMIC APPARATUS

(75) Inventor: Tokio Ueno, Nagoya (JP)

(73) Assignee: NIDEK Co., Ltd., Gamagori-shi (JP)

( * ) Notice: Subject to any disclaimer, the term of this patent is extended or adjusted under 35 U.S.C. 154(b) by 415 days.

(21) Appl. No.: 11/605,957

(22) Filed: Nov. 30, 2006

(65) Prior Publication Data

US 2007/0127033 A1 Jun. 7, 2007

(30) Foreign Application Priority Data

Nov. 30, 2005 (JP) .............................. 2005-347288

(51) Int. Cl.
*G01B 11/02* (2006.01)
*G01B 9/02* (2006.01)
*G01J 3/45* (2006.01)

(52) U.S. Cl. ........................ 356/479; 356/497; 356/451; 356/508

(58) Field of Classification Search .................. 356/451, 356/456, 400, 508, 479, 497
See application file for complete search history.

(56) References Cited

U.S. PATENT DOCUMENTS

| | | | |
|---|---|---|---|
| 5,501,226 A * | 3/1996 | Petersen et al. ............. | 600/504 |
| 5,537,162 A | 7/1996 | Hellmuth et al. | |
| 5,847,806 A | 12/1998 | Mihashi | |
| 6,377,349 B1 * | 4/2002 | Fercher ........................ | 356/497 |
| 7,248,907 B2 * | 7/2007 | Hogan .......................... | 600/316 |
| 7,480,058 B2 * | 1/2009 | Zhao et al. ................... | 356/497 |
| 2006/0066869 A1 * | 3/2006 | Ueno et al. ................... | 356/497 |
| 2007/0222945 A1 * | 9/2007 | Tsukada et al. .............. | 351/205 |

FOREIGN PATENT DOCUMENTS

| | | |
|---|---|---|
| JP | A 10-033484 | 2/1998 |
| JP | A 11-325849 | 11/1999 |
| JP | A 2004-028970 | 1/2004 |

* cited by examiner

*Primary Examiner*—Patrick J Connolly
(74) *Attorney, Agent, or Firm*—Oliff & Berridge, PLC

(57) ABSTRACT

An apparatus using optical coherence tomography based on spectral interference and an ophthalmic apparatus, which can accurately obtain information on an object in a depth direction by correcting misalignment between an optical member of a spectral optical system and a photodetector, includes an interference optical system for irradiating measurement light being low coherent light onto the object and synthesizing the measurement light reflected from the object and reference light being low coherent light to interfere, a spectral optical system which disperses interference light for every frequency, a photodetector photo-receiving the dispersed interference light, means guiding calibration light for adjusting alignment between the spectral optical system and the photodetector to the spectral optical system, means storing reference spectral information, and means adjusting the alignment based on a comparison between spectral information on the calibration light guided to the spectral optical system and photo-received on the photodetector, and the stored information.

7 Claims, 3 Drawing Sheets reference spectral information

APPARATUS USING OPTICAL COHERENCE TOMOGRAPHY BASED ON SPECTRAL INTERFERENCE, AND AN OPHTHALMIC APPARATUS

BACKGROUND OF THE INVENTION

1. Field of the Invention

The present invention relates to an apparatus for obtaining information on an object in a depth direction using optical coherence tomography (OCT) based on spectral interference (using spectral interference), and specifically, relates to an ophthalmic apparatus for obtaining information on an eye in a depth direction.

2. Description of Related Art

There is an apparatus for obtaining information on an object in a depth direction, including a tomographic image, a surface image, a shape and a size of the object, using optical coherence tomography based on spectral interference. This kind of apparatus, for example, obtains the information on the object in the depth direction by irradiating measurement light (object light) being low coherent light onto the object, synthesizing the measurement light reflected from the object and reference light being low coherent light to interfere by an interference optical system, dispersing interference light for every frequency (wavelength) by a spectral optical system, photo-receiving the dispersed interference light with a photodetector and analyzing a photo-receiving signal thereof (see U.S. Pat. No. 6,377,349 corresponding to Japanese Patent Application Unexamined Publication No. HEI11-325849).

By the way, in the above-mentioned apparatus, as for the photodetector which photo-receives the interference light dispersed into frequency components, a predetermined correlation is established between its pixels and the frequency components (for example, the frequency components to be photo-received are allocated to every pixel of the photodetector). However, if there occurs misalignment between an optical member such as a diffraction grating of the spectral optical system and the photodetector, spectral information (light intensity distribution information) detected by the photodetector is changed; therefore, there is a possibility that the information on the object in the depth direction cannot be accurately obtained.

SUMMARY OF THE INVENTION

An object of the invention is to overcome the problems described above and to provide an apparatus using optical coherence tomography based on spectral interference which can accurately obtain information on an object in a depth direction by correcting misalignment between an optical member of a spectral optical system and a photodetector, and to provide an ophthalmic apparatus.

To achieve the objects and in accordance with the purpose of the present invention, an apparatus for obtaining information on an object in a depth direction using optical coherence tomography based on spectral interference includes an interference optical system for irradiating measurement light being low coherent light onto the object and synthesizing the measurement light reflected from the object and reference light being low coherent light to interfere, a spectral optical system for dispersing interference light by the interference optical system for every frequency, a photodetector which photo-receives the interference light dispersed by the spectral optical system, light guiding means which guides calibration light for adjusting alignment between the spectral optical system and the photodetector to the spectral optical system, storage means which stores reference spectral information, adjustment means which adjusts the alignment between the spectral optical system and the photodetector based on a comparison between spectral information on the calibration light photo-received on the photodetector guided by the spectral optical system and the reference spectral information stored in the storage means.

Additional objects and advantages of the invention are set forth in the description which follows, are obvious from the description, or may be learned by practicing the invention. The objects and advantages of the invention may be realized and attained by the apparatus in the claims.

BRIEF DESCRIPTION OF THE DRAWINGS

The accompanying drawings, which are incorporated in and constitute apart of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
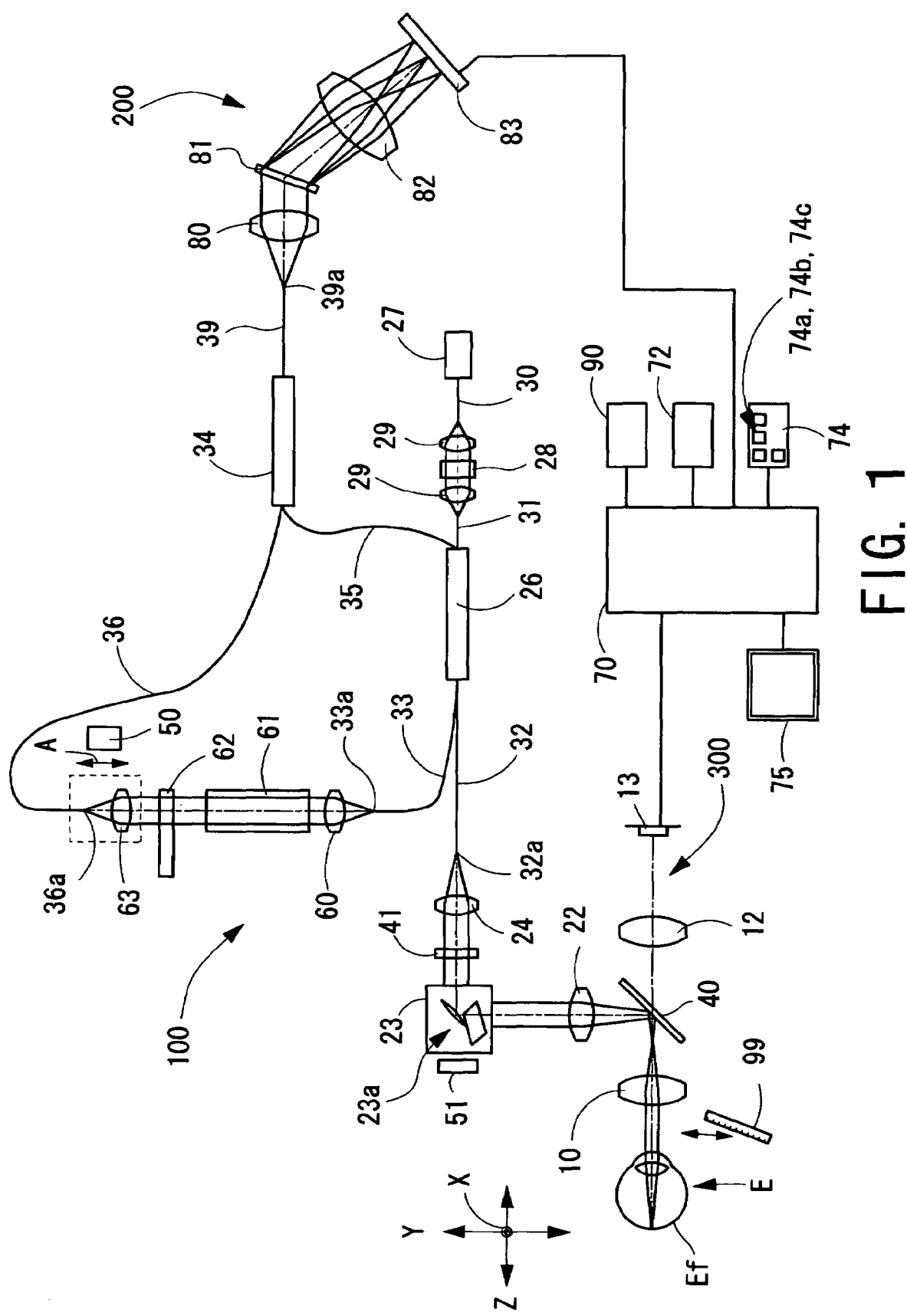
FIG. 1 is a view showing a schematic configuration of an optical system and a control system of an ophthalmic apparatus consistent with one preferred embodiment of the present invention.

A detailed description of one preferred embodiment of an apparatus using optical coherence tomography based on spectral interference, and an ophthalmic apparatus embodied by the present invention is provided below with reference to the accompanying drawings. FIG. 1 is a view showing a schematic configuration of an optical system and a control system of an ophthalmic OCT apparatus based on spectral interference (using spectral interference) consistent with one preferred embodiment of the present invention. It should be noted that the apparatus consistent with the preferred embodiment is an apparatus for obtaining a tomographic image of a fundus Ef of an examinee's eye E as an object. In addition, in the preferred embodiment, a depth direction of the eye E is referred to as a Z-direction, a horizontal direction orthogonal to the depth direction is referred to as an X-direction, and a vertical direction is referred to as a Y-direction.

The optical system of the apparatus includes an interference optical system 100 for irradiating measurement light (object light) being low coherent light onto the eye E (the fundus Ef) and synthesizing the measurement light reflected from the eye E (the fundus Ef) and reference light being low coherent light to interfere, a spectral optical system 200 for dispersing interference light for every frequency (wavelength), a photodetector (a one-dimensional photodetector in the preferred embodiment) 83 which photo-receives the dispersed interference light, and a fundus observation optical system 300 for obtaining a front (surface) image of the fundus Ef for observation.

A description will be given to the interference optical system 100. An infrared light source 27 such as a super luminescent diode (SLD) is a light source which emits low coherent light used as measurement light and reference light, for example, a light source having a band of 50 nm with a center wavelength of 840 nm (a range with wavelengths of 815 to 865 nm). Infrared light from the light source 27 passes through an optical fiber 30 being a light guide, passes through collimator lenses 29 and an isolator 28 arranged therebetween, passes through an optical fiber 31 being a light guide, and enters a fiber coupler 26 being a light-dividing member to be divided into the measurement light and the reference light.

On an optical path of the measurement light from the fiber coupler 26 to the fundus Ef, arranged are an optical fiber 32 being a light guide, a relay lens 24 which is movable in a direction of an optical axis in accordance with refractive power of the eye E, optical path length correcting glass 41 for adjusting an optical path length of the measurement light, a scanning unit 23, a relay lens 22, a dichroic mirror 40 having properties of reflecting the measurement light of the interference optical system 100 and transmitting observation light of the fundus observation optical system 300, and an objective lens 10. In addition, on an optical path of the measurement light from the fundus Ef to the spectral optical system 200, arranged are the objective lens 10 to the fiber coupler 26, an optical fiber 35 being a light guide, a fiber coupler 34 being an optical coupling member, and an optical fiber 39 being a light guide. An end 32a of the optical fiber 32 is arranged in a position conjugate with the fundus Ef. The scanning unit 23 includes a pair of galvano mirrors 23a, which are made swingable (rotatable) by a driving mechanism part 51 to scan the measurement light in the X- and/or Y-directions. Further, reflective surfaces of the galvano mirrors 23a are arranged in positions conjugate with a pupil of the eye E (in the preferred embodiment, arranged to have a conjugate positional relationship between an intermediate position of the galvano mirrors 23a and the pupil).

The measurement light passing through the optical fiber 32 and projected from the fiber end 32a thereof, passes through the relay lens 24 and the optical path length correcting glass 41, is reflected by the galvano mirrors 23a, passes through the relay lens 22, is reflected by the dichroic mirror 40, passes through the objective lens 10, and converges at the fundus Ef. The measurement light reflected from the fundus Ef enters the fiber end 32a via the objective lens 10 to the relay lens 24, passes through the optical fiber 32, the fiber coupler 26 and the optical fiber 35, and enters the fiber coupler 34.

On the other hand, on an optical path of the reference light from the fiber coupler 26 to the spectral optical system 200, arranged are an optical fiber 33 being a light guide, a collimator lens 60, an optical path length correcting glass 61 for adjusting an optical path length of the reference light, an attenuating filter 62 for approximately equalizing light intensity of the reference light when entering the fiber coupler 34 with light intensity of the measurement light, a focusing lens 63, an optical fiber 36 being a light guide, the fiber coupler 34, and the optical fiber 39. The optical path length correcting glass 61 is used for correcting the optical path length of the reference light in accordance with a change of the optical path length of the measurement light, which is caused by the measurement light passing through the objective lens 10, the relay lens 22 and the relay lens 24. Besides, the optical path length correcting glass 41 is used for correcting the optical path length of the measurement light in accordance with a change of the optical path length of the reference light, which is caused by the reference light passing through the attenuating filter 62.

The focusing lens 63 and an end 36a of the optical fiber 36 are made movable in a direction of an optical axis (in a direction of an arrow A) by a driving mechanism part 50 to change the optical path length of the reference light. Accordingly, compared with a conventional method by which a reference mirror is moved in a direction of an optical axis, a configuration can be simplified. Needless to say, the conventional method may be employed.

The reference light passing through the optical fiber 33 and projected from the fiber end 33a thereof, passes through the collimator lens 60, the optical path length correcting glass 61, the attenuating filter 62 and the focusing lens 63, enters the fiber end 36a, passes through the optical fiber 36, and enters the fiber coupler 34.

The measurement light and the reference light entering the fiber coupler 34, are synthesized to be the interference light, which passes through the optical fiber 39 and is projected from an end 39a thereof, and enters the spectral optical system 200.

The spectral optical system 200 and the photodetector 83 will be described. The spectral optical system 200 includes a collimator lens 80, a diffraction grating (or a dispersing prism and the like) 81 for dispersing the interference light for every frequency (wavelength), and a condenser lens 82. The photodetector 83 photo-receives the interference light dispersed into frequency components. The interference light projected from the fiber end 39a, passes through the collimator lens 80, the diffraction grating 81 and the condenser lens 82 to be photo-received on the photodetector 83. A photo-receiving signal from the photodetector 83 is inputted into a control part 70. Spectral interference fringes (a power spectrum) are recorded on the photodetector 83, and since there exists a relationship of Fourier transform between the spectral interference fringes and correlation function, the control part 70 performs Fourier transform on the spectral interference fringes obtained by the photodetector 83, thereby obtaining mutual correlation function between the measurement light and the reference light, and obtaining information on the fundus Ef in the Z-direction.

Figure 2:
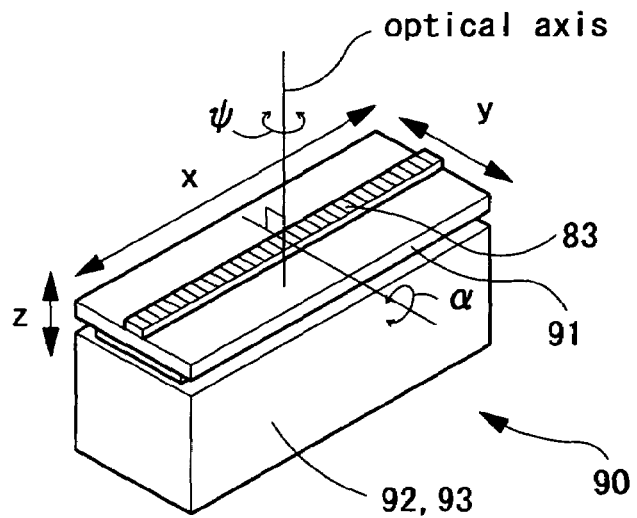
FIG. 2 is a view showing a schematic configuration of a positional adjustment mechanism part of a photodetector.

A description will be given to a positional adjustment mechanism part 90 which adjusts a position of the photodetector 83 with respect to the spectral optical system 200. FIG. 2 is a view of a schematic configuration of the positional adjustment mechanism part 90. The positional adjustment mechanism part 90 includes a stage 91 on which the photodetector 83 is mounted, a linear movement mechanism part 92 which linearly moves the stage 91 in three directions of x, y, and z, and a rotation mechanism part 93 which rotates the stage 91 in two directions of $\phi$ and $\alpha$. Besides, the z-direction corresponds to a direction of an optical axis of the spectral optical system 200, and the x- and y-directions correspond to a direction orthogonal to the optical axis of the spectral optical system 200. Further, in consideration of a size per pixel of the photodetector 83, preferably used as the positional adjustment mechanism part 90 is one which is capable of performing positional adjustment in increments of a few μm or a few nm, for example, used is one by which a minimum increment of the linear movement is 1 μm and a minimum increment of the rotation is 2 minites. In addition, for the positional adjustment mechanism part 90, a piezo-element, a stepping motor and the like are used to enable precise positional adjustment.

The fundus observation optical system 300 will be described. The fundus observation optical system 300 includes the objective lens 10, an image-pickup lens 12 and a two-dimensional image-pickup element 13. Reflection light from the fundus Ef illuminated by infrared light by an unillustrated illumination optical system, passes through the objective lens 10, the dichroic mirror 40 and the image-pickup lens 12 to form an image on the image-pickup element 13. An image-pickup signal from the image-pickup element 13 is inputted into the control part 70. The control part 70 controls to display the obtained front image of the fundus Ef on a monitor 75.

In addition, the control part 70 is connected with the light source 27, the photodetector 83, the positional adjustment mechanism part 90, the driving mechanism part 50, the driving mechanism part 51, the image-pickup element 13, a memory 72, a switch part 74, the monitor 75 and the like. The memory 72 stores the obtained image, reference spectral information which is information for performing positional adjustment (calibration) of the photodetector 83, and the like. The switch part 74 has a measurement starting switch 74a, a tomographic image obtaining position setting switch 74b and an auto-coherence switch 74c.

An operation of the apparatus having the aforementioned configuration will be described.

A description will be given to the positional adjustment of the photodetector 83 by the positional adjustment mechanism part 90. In the preferred embodiment, the reference light is used as light for calibration (hereinafter referred to as calibration light). Therefore, by an unillustrated driving mechanism part, a shielding plate 99 is inserted into the optical path through which the measurement light passes (in the preferred embodiment, between the dichroic mirror 40 and the eye E). Accordingly, the measurement light is prevented from entering the spectral optical system 200.

When power is applied to the apparatus, the control part 70 controls to light the light source 27. The infrared light from the light source 27 is divided into the measurement light and the reference light, and the measurement light is projected from the fiber end 32a. By the insertion of the shielding plate 99 into the optical path, the measurement light reflected from the fundus Ef is prevented from entering the fiber end 32a. Accordingly, only the reference light is photo-received on the photodetector 83 via the spectral optical system 200.

The control part 70 controls to perform the positional adjustment of the photodetector 83 based on spectral information obtained by photo-receiving only the reference light with the photodetector 83 and the reference spectral information stored in the memory 72 in advance. In the preferred embodiment, used as the reference spectral information is spectral information where there is a predetermined correlation between the pixels of the photodetector 83 and the frequency components, which is detected by the photodetector 83 when the optical members provided in the spectral optical system 200 are properly arranged. More specifically, used is spectral information where the frequency components photo-received are allotted to every pixel of the photodetector 83, and proper light intensity can be obtained for every pixel of the photodetector 83. In this case, information which is equivalent to spectral information on low coherent light from the light source 27 can be also used as the reference spectral information.

Figure 4:
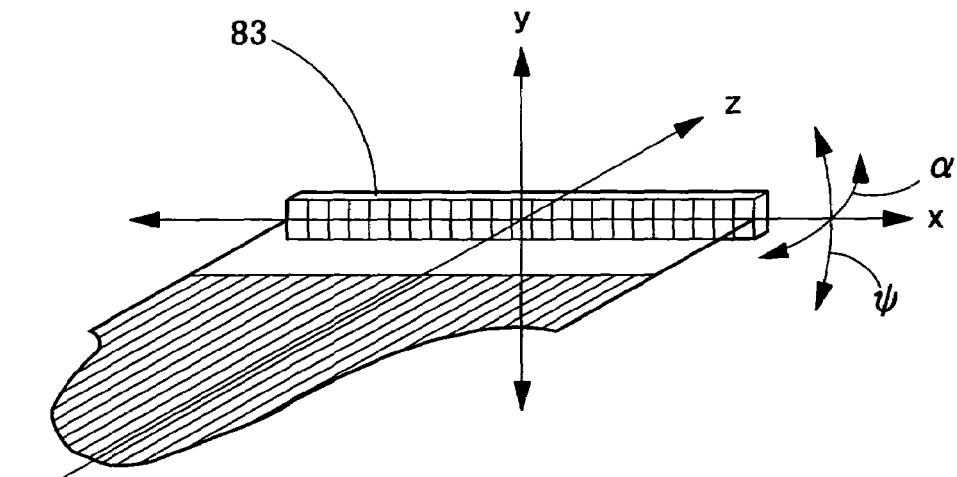
FIG. 4 is a view for illustrating a method of adjusting a position of the photodetector.

A basic idea in performing the positional adjustment of the photodetector 83 will be described. As shown in FIG. 4, the direction of the optical axis of the spectral optical system 200 is referred to as the z-direction, a direction orthogonal to the z-direction, which corresponds to the longitudinal direction of the photodetector 83 arranged in a position where the reference spectral information can be detected (a position after the completion of the calibration) is referred to as the x-direction, a direction orthogonal to the x- and z-directions is referred to as the y-direction, a direction having the optical axis of the spectral optical system 200 as a rotation center is referred to as the φ-direction, and a direction having an axis in the y-direction orthogonal to the optical axis of the spectral optical system 200 as a rotation center is referred to as the α-direction. Besides, the photodetector 83 is provided on the stage 91 so that a photo-receiving surface thereof is opposed to the condenser lens 82.

Figure 3:
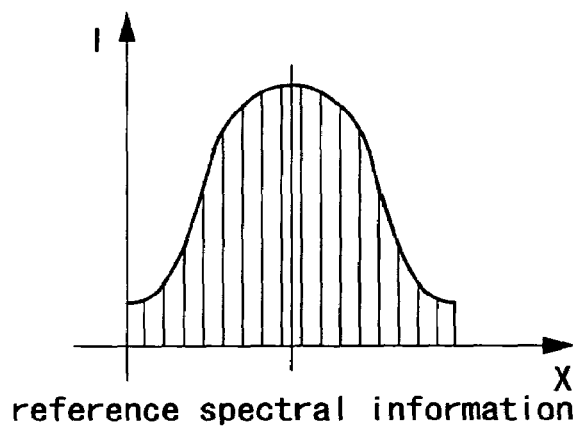
FIG. 3 is a view for showing an example of reference spectral information.

Here, as compared to the reference spectral information stored in the memory 72 (see FIG. 3) if a waveform of the spectral information detected by the photodetector 83 is unequal, the control part 70 drives the linear movement mechanism part 92 to move the photodetector 83 in the z-direction. When the photodetector 83 is moved in the z-direction, the waveform of the detected spectral information changes; therefore, the control part 70 controls to move the photodetector 83 in the z-direction so as to make the waveform of the detected spectral information closer to the waveform of the reference spectral information.

In addition, as compared to the reference spectral information stored in the memory 72 if the waveform of the spectral information detected by the photodetector 83 is approximately equal but total intensity is unequal (is smaller), the control part 70 drives the linear movement mechanism part 92 to move the photodetector 83 in the y-direction. When the photodetector 83 is moved in the y-direction, the total intensity of the detected spectral information changes, and therefore, the control part 70 controls to move the photodetector 83 in the y-direction so as to make the total intensity of the detected spectral information (peak intensity) closer to the total intensity of the reference spectral information (peak intensity).

Further, as compared to the reference spectral information stored in the memory 72 if the waveform and the total intensity of the spectral information detected by the photodetector 83 are approximately equal but a pixel position where the peak intensity is detected is unequal, the control part 70 drives the linear movement mechanism part 92 to move the photodetector 83 in the x-direction. When the photodetector 83 is moved in the x-direction, the peak detecting position of the detected spectral information is shifted; therefore, the control part 70 controls to move the photodetector 83 in the x-direction so as to make the peak detecting position of the detected spectral information closer to the peak detecting position of the reference spectral information (so as to detect the peak intensity with preset pixels of the photodetector 83).

In addition, as compared to the reference spectral information stored in the memory 72 if intensity in a certain frequency range of the spectral information detected by the photodetector 83 is approximately equal (not attenuated) and the intensity in the other frequency range is unequal (is attenuated), the control part 70 drives the rotation mechanism part 93 to rotate the photodetector 83 in the φ-direction or in the α-direction. When the photodetector 83 is rotated, the waveform of the detected spectral information changes, and therefore, the control part 70 controls to rotate the photodetector 83 so as to make the waveform of the detected spectral information closer to the waveform of the reference spectral information.

Figure 5:
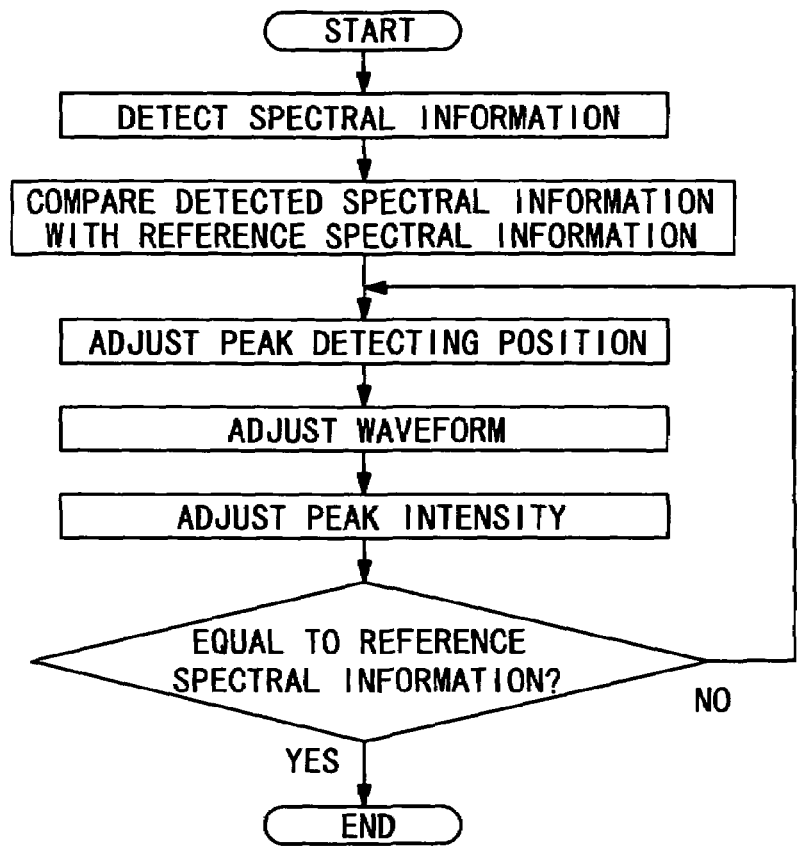
FIG. 5 is a flowchart for showing an example when adjusting the position of the photodetector.

Here, since misalignment between the spectral optical system 200 and the photodetector 83 is not always found in only one direction, in the preferred embodiment, the positional adjustment of the photodetector 83 is performed as follows (see FIG. 5). The control part 70 controls to compare the spectral information detected by the photodetector 83 with the reference spectral information stored in the memory 72.

Then, based on a result of the comparison, first, the control part 70, by linearly moving and rotating the photodetector 83, performs positional adjustment of the photodetector 83 so as to make the peak detecting position of the detected spectral information closer to the peak detecting position of the reference spectral information. Next, the control part 70, by linearly moving and rotating the photodetector 83, performs positional adjustment of the photodetector 83 so as to make the waveform of the detected spectral information closer to the waveform of the reference spectral information. Next, the control part 70, by linearly moving the photodetector 83, performs positional adjustment of the photodetector 83 so as to make the peak intensity of the detected spectral information closer to a predetermined intensity level. Besides, if the positional adjustment of the photodetector 83 is performed as mentioned above and the detected spectral information does not coincide with the reference spectral information, a step returns to an adjustment of the peak detecting position.

Thus, when the spectral information detected by the photodetector 83 is judged as equal to the reference spectral information stored in the memory 72 by performing the positional adjustment of the photodetector 83, the control part 70 controls to judge that the photodetector 83 is arranged so that the correlation between the pixels of the photodetector 83 and the frequency components is in a proper state for obtaining the tomographic image of the fundus Ef, then goes to a step to obtain the tomographic image of the fundus Ef.

The obtainment of the tomographic image of the fundus Ef will be briefly described. When an image of an anterior segment of the eye E by an unillustrated anterior-segment observation optical system is displayed on the monitor 75, alignment of the apparatus with respect to the eye E is performed so that the front image of the fundus Ef by the fundus observation optical system 300 is displayed on the monitor 75. When the front image of the fundus Ef is displayed on the monitor 75 (see FIG. 6), focusing is obtained on the fundus Ef.

Next, when the auto-coherence switch 74c is operated, the control part 70 drives the driving mechanism part 50 to integrally move the fiber end 36a and the focusing lens 63.

Next, when the measurement starting switch 74a is operated, the control part 70 drives the driving mechanism part 51 to move the measurement light in the X- and Y-directions (two-dimensionally) by the galvano mirrors 23a. The control part 70 controls to obtain information on the fundus Ef in the Z-direction based on the photo-receiving signal (an interference signal) from the photodetector 83 obtained in synchronization with the scanning of the measurement light in the X- and Y-directions, thereby obtaining a three-dimensional tomographic image of the fundus Ef.

Figures 6, 7:
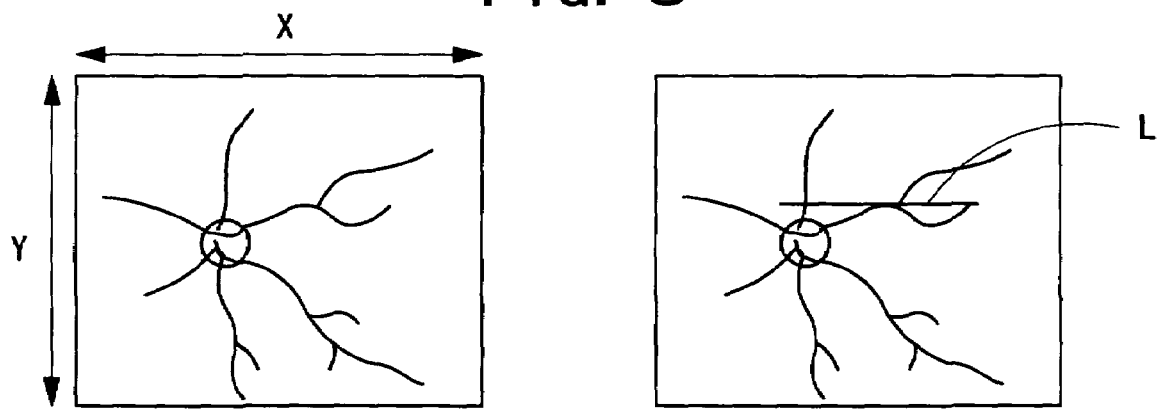
FIG. 6 is a view showing an example of displaying a front image of a fundus.
FIG. 7 is a view showing an example in which a line indicating a position to obtain a tomographic image of the fundus is displayed on the front image of the fundus.
Figure 8:
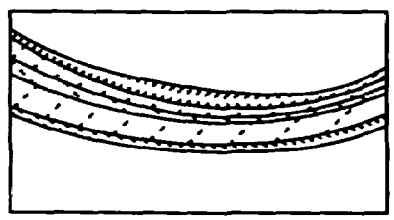
FIG. 8 is a view showing an example of displaying the tomographic image on the fundus.

The control part 70 controls to obtain a two-dimensional front (surface) image of the fundus Ef for observation from the obtained three-dimensional tomographic image of the fundus Ef and display the obtained two-dimentional image on the monitor 75 along with a line L for setting a position to obtain a two-dimensional tomographic image of the fundus Ef (see FIG. 7). When the obtaining position is set by operating the setting switch 74b, the control part 70 controls to obtain the two-dimensional tomographic image of the fundus Ef corresponding to the set obtaining position from the three-dimensional tomographic image of the fundus Ef, to display on the monitor 75 (see FIG. 8).

As described above, by making the photodetector 83 move with respect to the spectral optical system 200, moving only the photodetector 83 can correct the misalignment between the spectral optical system 200 and the photodetector 83.

Incidentally, the optical members of the spectral optical system 200 may be moved with respect to the photodetector 83, instead of moving the photodetector 83 with respect to the spectral optical system 200. In other words, it is essential only that alignment between the spectral optical system 200 and the photodetector 83 can be adjusted. In the configuration of the preferred embodiment, for example, it is also preferable that the diffraction grating 81 is rotated in the φ-direction, and the condenser lens 82 is linearly moved in the x-, y- and z-directions and is rotated in the α-direction.

In addition, when proper spectral information can not be detected, or when the spectral information detected by the photodetector 83 does not coincide with the reference spectral information stored in the memory 72, the control part 70 may control to show a message informing that there is the misalignment between the spectral optical system 200 and the photodetector 83 (for example, to display the message on the monitor 75).

Further, it is also preferable that a dedicated mode for performing the above-mentioned positional adjustment (calibration) is provided, and the positional adjustment is performed by operating a mode setting switch included in the switch part 74. In this case, the shielding plate 99 may be inserted into the optical path of the measurement light in response to the operation of the mode setting switch.

Furthermore, the reference light from the light source 27 is used as the calibration light; however, it is not limited thereto, and, for example, the calibration light from a dedicated light source may be directed to the spectral optical system 200.

In addition, since there is a possibility that the spectral information on the light from the light source may change in accordance with time-varying change of the light source for the positional adjustment (the calibration), it is preferable to measure the spectral information on the light from the light source by using a spectrum radiometer or the like. For example, if the spectral information on the light from the light source 27 is measured and the measured spectral information is used as the reference spectral information in performing positional adjustment of the photodetector 83, the information on the eye E in the depth direction can be obtained more accurately.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An apparatus for obtaining information on an object in a depth direction using optical coherence tomography based on spectral interference, the apparatus comprising:

an interference optical system for irradiating measurement light being low coherent light onto the object and synthesizing the measurement light reflected from the object and reference light being low coherent light to interfere;

a spectral optical system for dispersing interference light by the interference optical system for every frequency;

a photodetector which photo-receives the interference light dispersed by the spectral optical system;

light guiding means which guides calibration light for adjusting alignment between the spectral optical system and the photodetector to the spectral optical system;

storage means which stores reference spectral information; and adjustment means which adjusts the alignment between the spectral optical system and the photodetector, based on a comparison between spectral information on the calibration light guided to the spectral optical system and photo-received on the photodetector, and the reference spectral information stored in the storage means.

2. The apparatus according to claim 1, wherein the light guiding means guides only the reference light as the calibration light to the spectral optical system via the interference optical system.

3. The apparatus according to claim 2, wherein the light guiding means includes limiting means which prevents the measurement light from being guided to the spectral optical system via the interference optical system.

4. The apparatus according to claim 1, wherein the adjustment means adjusts a position of the photodetector with respect to the spectral optical system.

5. The apparatus according to claim 4, wherein the adjustment means includes moving means which linearly moves the photodetector in a direction of an optical axis of the spectral optical system and in a direction orthogonal to the optical axis.

6. The apparatus according to claim 4, wherein the adjustment means includes rotation means which rotates the photodetector in a direction having the optical axis of the spectral optical system as a rotation center.

7. The apparatus according to claim 1, wherein the object is an eye.

* * * * *